United States Patent
Lo et al.

(10) Patent No.: US 12,397,285 B2
(45) Date of Patent: Aug. 26, 2025

(54) PROCESS FOR CONVERTING CARBON OXIDE INTO METHANOL

(71) Applicant: INDUSTRIAL TECHNOLOGY RESEARCH INSTITUTE, Hsinchu (TW)

(72) Inventors: Man-Yin Lo, Zhubei (TW); Yen-Chih Chen, Changhua (TW); Nai-Chia Cheng, New Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 18/497,872

(22) Filed: Oct. 30, 2023

(65) Prior Publication Data
US 2024/0058799 A1 Feb. 22, 2024

Related U.S. Application Data

(63) Continuation-in-part of application No. 16/895,202, filed on Jun. 8, 2020, now abandoned.

(30) Foreign Application Priority Data

Dec. 26, 2019 (TW) ................. 108147789

(51) Int. Cl.
*B01J 23/89* (2006.01)
*B01J 23/44* (2006.01)
*C07C 29/154* (2006.01)
*C07C 29/157* (2006.01)
*C07C 31/04* (2006.01)

(52) U.S. Cl.
CPC ........... *B01J 23/8953* (2013.01); *B01J 23/44* (2013.01); *C07C 29/154* (2013.01); *C07C 29/157* (2013.01); *C07C 31/04* (2013.01)

(58) Field of Classification Search
CPC .......................................... C07C 29/153–158
See application file for complete search history.

(56) References Cited

U.S. PATENT DOCUMENTS

| | | | |
|---|---|---|---|
| 4,596,782 A | 6/1986 | Courty et al. | |
| 6,048,820 A | 4/2000 | Takeuchi et al. | |
| 8,623,782 B2 | 1/2014 | Murakami et al. | |
| 8,889,089 B2 | 11/2014 | Aasberg-Petersen et al. | |
| 10,265,681 B2 | 4/2019 | Mitchell et al. | |
| 2013/0237618 A1* | 9/2013 | Matsushita | C07C 29/154 518/713 |
| 2019/0184379 A1* | 6/2019 | Lo | B01J 37/04 |

FOREIGN PATENT DOCUMENTS

| | | |
|---|---|---|
| CN | 101384363 A | 3/2009 |
| CN | 101386564 A | 3/2009 |
| CN | 102240553 A | 11/2011 |
| CN | 102302934 A | 1/2012 |
| CN | 103933978 A | 7/2014 |
| CN | 105013492 A | 11/2015 |
| CN | 103459020 B | 8/2016 |
| CN | 104379255 B | 5/2017 |
| TW | I465393 B | 12/2014 |

OTHER PUBLICATIONS

Liang et al., "Carbon nanotube-supported Pd—ZnO catalyst for hydrogenation of CO2 to methanol", Elsevier, Applied Catalysis B: Environmental, vol. 88, (2009), p. 315-322.
Martin, O. et al. "Zinc-Rich Copper Catalysts Promoted by Gold for Methanol Synthesis" ACS Catalysis 2015, 5, 5607-5616 (Year: 2015).
Taiwanese Office Action and Search Report for Taiwanese Application No. 108147789, dated Nov. 4, 2020.
Wu et al., "Optimization of preparation conditions and improvement of stability of Cu/ZnO-based multicomponent catalysts for methanol synthesis from CO2 and H2", Elsevier, Catalysis Today, (1998), pp. 215-220.

* cited by examiner

*Primary Examiner* — Medhanit W Bahta
(74) *Attorney, Agent, or Firm* — Birch, Stewart, Kolasch & Birch, LLP

(57) ABSTRACT

A process of utilizing the catalyst for converting carbon oxide into methanol is provided. The process includes putting a catalyst into a fixed bed reactor and introducing a gas mixture of hydrogen and the carbon oxide into the fixed bed reactor, and performing a hydrogenation reaction under the effect of the catalyst to form the methanol

8 Claims, No Drawings

PROCESS FOR CONVERTING CARBON OXIDE INTO METHANOL

CROSS REFERENCE TO RELATED APPLICATIONS

This application claims the benefit of Taiwan Patent Application No. 108147789, filed Dec. 26, 2019, the entirety of which is incorporated by reference herein. This application is a Continuation-in-Part of U.S. patent application Ser. No. 16/895,202, filed Jun. 8, 2020 and entitled "Catalyst and process for converting carbon oxide into methanol".

TECHNICAL FIELD

Embodiments of the present disclosure relate to a process of utilizing the catalyst for converting carbon oxide into methanol.

BACKGROUND

Carbon dioxide ($CO_2$) is a greenhouse gas, and carbon dioxide reduction may be achieved by mitigating emissions and lowering the environmental concentration. In addition, carbon dioxide may be converted into chemicals or fuels, which not only mitigates carbon dioxide emission but also moderates the dependence on the fossil raw materials or renewable energy. Therefore, the carbon capture and utilization (CCU) should be more efficient to mitigate carbon dioxide emissions.

Methanol is widely utilized in several fields that may serve directly as liquid fuel for internal combustion engines and methanol fuel cells. However, converting carbon dioxide into methanol is ineffective in today's industry. One major reason that the methanol yield cannot be enhanced is thermodynamic limitation. For example, when a general catalyst is used to convert carbon dioxide into methanol, the reaction temperature is higher (e.g., higher than 250° C.), resulting in an inefficient process (i.e., a low conversion rate), and greater energy consumption.

Therefore, a process for converting carbon dioxide into methanol and a related catalyst is called for. The activity and efficiency of converting carbon dioxide into methanol may be enhanced by collocating the process and catalyst.

SUMMARY

Embodiments of the present disclosure provide a catalyst for converting carbon oxide into methanol and a process of utilizing the catalyst for converting carbon oxide into methanol, which may effectively increase the conversion rate from carbon dioxide to methanol at a lower reaction temperature, thereby improving the overall efficiency of the process and reducing energy consumption.

In accordance with some embodiments of the present disclosure, a catalyst for converting carbon oxide into methanol is provided. The catalyst includes 40-60 parts by weight of Cu, 25-40 parts by weight of Zn, 2-15 parts by weight of Al, 0.1-3 parts by weight of Si, and a metal. The metal includes Pd or Au, and the Pd and the Au are independently 0.1-5 wt % based on the total weight of Cu, Zn, Al, and Si in the catalyst, wherein the total weight of Cu, Zn, Al, Si, and Pd or the total weight of Cu, Zn, Al, Si and Au are 100 parts by weight.

In accordance with some other embodiments of the present disclosure, a process for converting carbon oxide into methanol is provided. The process for converting carbon oxide into methanol includes putting the described catalyst into a fixed bed reactor. The process for converting carbon oxide into methanol further includes introducing a gas mixture of hydrogen and the carbon oxide into the fixed bed reactor, and performing a hydrogenation reaction under the effect of the catalyst to form the methanol.

DETAILED DESCRIPTION

This disclosure provides different embodiments to illustrate the technical features of different implementations of this disclosure. For example, "one embodiment" or "some embodiments" referred to in the entire specification means that the specific features, structures, or characteristics described in the embodiments are included in at least one embodiment. Therefore, the phrases "in one embodiment" or "in some embodiments" appearing in different places in the entire specification do not necessarily refer to the same embodiment. In addition, the specific features, structures, or characteristics may be combined in any suitable method in one or more embodiments.

It should be understood that additional operations can be provided before, during, and after the method, and some of the operations described can be replaced or eliminated for other embodiments of the method.

In the present disclosure, the terms "about," "approximately" and "substantially" typically mean +/−20% of the stated value, more typically +/−10% of the stated value, more typically +/−5% of the stated value, more typically +/−3% of the stated value, more typically +/−2% of the stated value, more typically +/−1% of the stated value and even more typically +/−0.5% of the stated value. The stated value of the present disclosure is an approximate value. That is, when there is no specific description of the terms "about," "approximately" and "substantially", the stated value includes the meaning of "about," "approximately" or "substantially".

Unless otherwise defined, all terms (including technical and scientific terms) used herein have the same meaning as commonly understood through one of ordinary skill in the art to which this disclosure belongs. It should be understood that terms such as those defined in commonly used dictionaries should be interpreted as having a meaning that is consistent with their meaning in the context of the relevant art and will not be interpreted in an idealized or overly formal sense unless expressly so defined in the embodiments of the present disclosure.

According to some embodiments of the present disclosure, a catalyst for converting carbon oxide into methanol is provided. The catalyst is modified to increase the efficiency of converting the carbon oxide into the methanol in a single fixed bed reactor, thereby enhancing the methanol yield in a single reaction. Simultaneously, according to some other embodiments of the present disclosure, a process of converting carbon oxide into methanol is provided. By utilizing the aforementioned catalyst, it may effectively increase the conversion rate from carbon dioxide to methanol at a lower reaction temperature, thereby improving the overall efficiency of the process and reducing energy consumption.

According to one embodiment of the present disclosure, a catalyst for converting carbon oxide into methanol is provided. In some embodiments, the catalyst may include 35-65 parts by weight (e.g., 40-60 parts by weight) of Cu, 20-50 parts by weight (e.g., 25-40 parts by weight) of Zn, 2-20 parts by weight (e.g., 2-15 parts by weight) of Al, 0.1-5 parts by weight (e.g., 0.1-3 parts by weight) of Si, and a metal. The metal may include Pd or Au. That is, in some embodiments, the catalyst may be, for example, Cu—Zn—Al—Si—Pd or Cu—Zn—Al—Si—Au. In accordance with some embodiments of the present disclosure, a catalyst for converting carbon oxide into methanol is provided. The catalyst includes 40-60 parts by weight of Cu, 25-40 parts by weight of Zn, 2-15 parts by weight of Al, 0.1-3 parts by weight of Si, and a metal. The metal includes Pd or Au, and the Pd and the Au are independently 0.1-5 wt % based on the total weight of Cu, Zn, Al, and Si in the catalyst. The total weight of Cu, Zn, Al, Si, and Pd or the total weight of Cu, Zn, Al, Si and Au are 100 parts by weight.

In some embodiments, Pd and Au are independently 0.1-5 wt % based on the total weight of Cu, Zn, Al, and Si in the catalyst, such as 0.25-1 wt %, 0.25-3 wt %, 0.25-5 wt %, or 1-5 wt %, but the present disclosure is not limited thereto. If there is too much Pd or Au, it may result in the active center being covered, thereby lowering the catalyst activity. Moreover, Pd and Au are noble metals (precious metals), and if the content is too high, then the cost may be excessive. If the content of Pd or Au is too low, the resulting poor hydrogen activation effect may reduce the catalyst activity.

In some embodiments, the carbon oxide may include $CO_2$, CO, or a combination thereof. In some embodiments, the carbon oxide may be only $CO_2$ or CO. In some embodiments, the carbon oxide may include a gas mixture of $CO_2$ and CO. For example, the molar ratio of $CO_2$ to CO may be about 20/1 to 2/1, such as 10/1 to 10/3, but the present disclosure is not limited thereto.

In some embodiments, carbon oxide may be converted into methanol by a hydrogenation reaction. By introducing hydrogen ($H_2$), methanol may be synthesized from hydrogen and carbon oxide under the effect of the catalyst. The molar ratio of hydrogen to carbon oxide may be adjusted according to different types of catalyst and reaction conditions.

Because Pd or Au is beneficial to activate hydrogen and carbon oxide, the catalyst modified with Pd or Au in the embodiments of the present disclosure may enhance the conversion rate of $CO_2$ and the methanol selectivity, thereby dramatically enhance the methanol yield in a single reaction of converting the carbon oxide into methanol. The catalyst in the embodiments of the present disclosure may still efficiently enhance the methanol yield even if the content of $CO_2$ is high. In addition, during the process of producing methanol, by utilizing the catalyst provided by the present disclosure, the hydrogenation reaction may be carried out at a lower reaction temperature (e.g., the temperature of equipment in a general factory, about 180-250° C.). There is no need to provide additional thermal energy, thereby reducing production costs and process time, and improving efficiency of the process.

According to another embodiment of the present disclosure, a process for converting carbon oxide into methanol is provided. In some embodiments, the process may include putting the aforementioned catalyst into a fixed bed reactor, introducing a gas mixture of hydrogen ($H_2$) and the carbon oxide into the fixed bed reactor, and performing a hydrogenation reaction under the effect of the catalyst to form the methanol.

In some embodiments, the molar ratio of hydrogen to the carbon oxide may be about 3/1 to 10/1, but the present disclosure is not limited thereto. For example, the carbon oxide may be only $CO_2$. In this condition, the molar ratio $H_2/CO_2$ may be about 3/1 to 9/1, but the present disclosure is not limited thereto. In some embodiments, $H_2/CO_2$ with a molar ratio of about 3/1 may be introduced into the fixed bed reactor to perform the hydrogenation reaction under the effect of the catalyst, thereby converting $CO_2$ into methanol as shown in Formula (1):

$$CO_2 + 3H_2 \rightarrow CH_3OH + H_2O \qquad (1)$$

As shown in Formula (1), the byproduct of the hydrogenation reaction further includes $H_2O$. In some embodiments, the byproduct of the hydrogenation reaction further includes CO (not shown).

In this embodiment, the unreacted $CO_2$, $H_2$, and the byproduct CO may be recycled to be repeatedly used, so that they may be introduced into the fixed bed reactor to continue the hydrogenation reaction to convert the $CO_2$ and CO into methanol. Therefore, the cycle number of the exhaust produced from the hydrogenation reaction is reduced, the efficiency of the process of producing methanol is enhanced, and the manufacturing cost is lowered.

In some embodiments, the hydrogenation reaction may be performed at gas hourly space velocity (GHSV) of 3600-20000 $h^{-1}$. For example, the hydrogenation reaction may be performed at GHSV of 3600-7200 $h^{-1}$ or 7200-10000 $h^{-1}$, but the present disclosure is not limited thereto. A hydrogenation reaction performed at GHSV that is too low results in methanol production that is too low. A hydrogenation reaction performed at GHSV that is too high results in a $CO_2$ conversion rate that is too low.

In some embodiments, the hydrogenation reaction may be performed at a temperature of 180-250° C. That is, the reaction temperature may be 180-250° C. For example, the reaction temperature may be 200° C., 220° C., or 250° C., but the present disclosure is not limited thereto. A hydrogenation reaction performed at a temperature that is too low results in no reaction. A hydrogenation reaction performed at a temperature that is too high lowers the methanol selectivity and increases energy consumption.

In some embodiments, the hydrogenation reaction may be performed under a pressure of 30-80 $kg/cm^2$. For example, the hydrogenation reaction may be performed under a pressure of 40 $kg/cm^2$ or 70 $kg/cm^2$, but the present disclosure is not limited thereto. A hydrogenation reaction performed under a pressure that is too low results in a conversion rate of $CO_2$ that is too low. A hydrogenation reaction performed under a pressure that is too high may dramatically increase the manufacturing cost.

In order to make the above content and other purposes, features, and advantages of the present disclosure more obvious and understandable, the following embodiments and comparative examples are specifically given for detailed description.

Embodiments

[Catalyst I] Cu—Zn—Al—Si—Pd (Pd Content is 1 wt %)

54.3 g of $Cu(NO_3)_2$, 39.1 g of $Zn(NO_3)_2$, 6.6 g $Al(NO_3)_3$, and 0.95 g of Si were dissolved in 1500 mL of de-ionized water to form Liquid A. 140 g of $NaHCO_3$ was dissolved in 500 mL of de-ionized water to form Liquid B. Liquid A and Liquid B were added into 400 g of de-ionized water with constant stirring at an addition rate of 10 mL/min. After stirring for 24 hours, the mixture was filtered and a filter cake was obtained. Then, the filter cake was washed with de-ionized water several times to remove the sodium ions. The filter cake was baked at 110° C. and then calcinated at 600° C. to obtain catalyst precursor I. Catalyst precursor I was cooled down to room temperature, and 10 g of catalyst precursor I was put into a pear-shaped bottle. A solution of 0.211 g of $Pd(CH_3COO)_2$ was added to the pear-shaped bottle. The mixture was then dried in a rotary evaporator and then baked at 110° C. to obtain Catalyst I with a Pd content of about 1 wt %.

[Catalyst II] Cu—Zn—Al—Si—Au (Au Content is 1 wt %)

The aforementioned Liquid A and Liquid B were added into 400 g of de-ionized water with constant stirring at an addition rate of 10 mL/min. After stirring for 24 hours, the mixture was filtered and a filter cake was obtained. Then, the filter cake was washed with de-ionized water several times to remove the sodium ions. The filter cake was baked at 110° C. and then calcinated at 600° C. to obtain catalyst precursor I. Catalyst precursor I was cooled down to room temperature, and 10 g of catalyst precursor I was put into a pear-shaped bottle. A solution of 0.172 g of $HAuCl_4$ was added to the pear-shaped bottle. The mixture was then dried in a rotary evaporator and then baked at 110° C. to obtain Catalyst II with an Au content of about 1 wt %.

[Catalyst III] Cu—Zn—Al—Si—Pd (Pd Content is 0.5 wt %)

The aforementioned Liquid A and Liquid B were added into 400 g of de-ionized water with constant stirring at an addition rate of 10 mL/min. After stirring for 24 hours, the mixture was filtered and a filter cake was obtained. Then, the filter cake was washed with de-ionized water several times to remove the sodium ions. The filter cake was baked at 110° C. and then calcinated at 600° C. to obtain catalyst precursor I. Catalyst precursor I was cooled down to room temperature, and 10 g of catalyst precursor I was put into a pear-shaped bottle. A solution of 0.105 g of $Pd(CH_3COO)_2$ was added to the pear-shaped bottle. The mixture was then dried in a rotary evaporator and then baked at 110° C. to obtain Catalyst III with a Pd content of about 0.5 wt %.

[Catalyst IV] Cu—Zn—Al—Si—Pd (Pd Content is 0.25 wt %)

The aforementioned Liquid A and Liquid B were added into 400 g of de-ionized water with constant stirring at an addition rate of 10 mL/min. After stirring for 24 hours, the mixture was filtered and a filter cake was obtained. Then, the filter cake was washed with de-ionized water several times to remove the sodium ions. The filter cake was baked at 110° C. and then calcinated at 600° C. to obtain catalyst precursor I. Catalyst precursor I was cooled down to room temperature, and 10 g of catalyst precursor I was put into a pear-shaped bottle. A solution of 0.053 g of $Pd(CH_3COO)_2$ was added to the pear-shaped bottle. The mixture was then dried in a rotary evaporator and then baked at 110° C. to obtain Catalyst IV with a Pd content of about 0.25 wt %.

Comparative Examples

[Catalyst V] Cu—Zn—Al—Si

The aforementioned Liquid A and Liquid B were added into 400 g of de-ionized water with constant stirring at an addition rate of 10 mL/min. After stirring for 24 hours, the mixture was filtered and a filter cake was obtained. Then, the filter cake was washed with de-ionized water several times to remove the sodium ions. The filter cake was baked at 110° C. and then calcinated at 600° C. to obtain Catalyst V.

[Catalyst VI] Cu—Zn—Al—Si—Zr—Ga 54.3 g of $Cu(NO_3)_2$, 39.1 g of $Zn(NO_3)_2$, 6.6 g $Al(NO_3)_3$, 0.95 g of Si, 12 g of $Zr(NO_3)_4$, and 10 g of $Ga(NO_3)_2$ were dissolved in 1500 mL of de-ionized water to form Liquid A'. The aforementioned Liquid A' and Liquid B were added into 400 g of de-ionized water with constant stirring at an addition rate of 10 mL/min. After stirring for 24 hours, the mixture was filtered and a filter cake was obtained. Then, the filter cake was washed with de-ionized water several times to remove the sodium ions. The filter cake was baked at 110° C. and then calcinated at 600° C. to obtain Catalyst VI.

[Catalyst VII] Cu—Zn—Al—Si—In

The aforementioned Liquid A and Liquid B were added into 400 g of de-ionized water with constant stirring at an addition rate of 10 mL/min. After stirring for 24 hours, the mixture was filtered and a filter cake was obtained. Then, the filter cake was washed with de-ionized water several times to remove the sodium ions. The filter cake was baked at 110° C. and then calcinated at 600° C. to obtain catalyst precursor I. Catalyst precursor I was cooled down to room temperature, and 10 g of catalyst precursor I was put into a pear-shaped bottle. A solution of 0.026 g of $In(NO_3)_3$ was added to the pear-shaped bottle. The mixture was then dried in a rotary evaporator and then calcinated at 600° C. to obtain Catalyst VII with an In content of about 1 wt %.

[Catalyst VIII] Cu—Zn—Al—Si—Ce

The aforementioned Liquid A and Liquid B were added into 400 g of de-ionized water with constant stirring at an addition rate of 10 mL/min. After stirring for 24 hours, the mixture was filtered and a filter cake was obtained. Then, the filter cake was washed with de-ionized water several times to remove the sodium ions. The filter cake was baked at 110° C. and then calcinated at 600° C. to obtain catalyst precursor I. Catalyst precursor I was cooled down to room temperature, and 10 g of catalyst precursor I was put into a pear-shaped bottle. A solution of 0.031 g of $Ce(NO_3)_3$ was added to the pear-shaped bottle. The mixture was then dried in a rotary evaporator and then calcinated at 600° C. to obtain Catalyst VIII with a Ce content of about 1 wt %.

Examples or Comparative Examples of Converting $CO_2$ into Methanol by the Catalyst 3.65 g aforementioned catalysts were respectively loaded in the fixed bed reactor. Gas mixture of $H_2/CO_2$ was introduced into the fixed bed reactor, and the reaction conditions (e.g., gas hourly space velocity $(GHSV)(h^{-1})$, reaction temperature (T)(° C.), and reaction pressure $(P)(kg/cm^2)$) were tuned to perform hydrogenation reaction. The product compositions were analyzed by on-line gas chromatography (on-line GC) to calculate the $CO_2$ conversion rate (%), CO selectivity (%), methanol selectivity (%), and methanol yield (%), and the results were shown in Table 1 (Examples) and Table 2 (Comparative examples).

Methanol yield (%) is equal to $CO_2$ conversion rate (%) multiplied by methanol selectivity (%). The higher $CO_2$ conversion rate or the higher methanol selectivity means that the methanol yield is better. Because CO is not the desired product, the lower CO selectivity is better. NR means that no methanol is produced (i.e., unreacted). Except for Example 14, the molar ratios of $H_2$ to $CO_2$ of other Examples and Comparative examples are about 3/1, while the molar ratio of $H_2$ to $CO_2$ of Example 14 is about 9/1.

TABLE 1

| | | reaction conditions | | | $CO_2$ | selectivity | | methanol |
|---|---|---|---|---|---|---|---|---|
| | Catalyst | T (° C.) | GHSV ($h^{-1}$) | P ($kg/cm^2$) | conversion rate (%) | CO (%) | methanol (%) | yield (%) |
| Example 1 | I: Cu—Zn—Al—Si—Pd (Pd content: 1 wt %) | 250 | 10000 | 40 | 34.0 | 25.8 | 74.2 | 25.2 |
| Example 2 | I: Cu—Zn—Al—Si—Pd (Pd content: 1 wt %) | 220 | 10000 | 40 | 33.0 | 24.9 | 75.1 | 24.7 |
| Example 3 | I: Cu—Zn—Al—Si—Pd (Pd content: 1 wt %) | 200 | 10000 | 40 | 27.7 | 13.2 | 86.8 | 24.1 |
| Example 4 | I: Cu—Zn—Al—Si—Pd (Pd content: 1 wt %) | 180 | 10000 | 40 | 10.8 | 12.6 | 87.5 | 9.4 |
| Example 5 | II: Cu—Zn—Al—Si—Au (Au content: 1 wt %) | 250 | 10000 | 40 | 34.4 | 28.8 | 71.2 | 24.5 |
| Example 6 | II: Cu—Zn—Al—Si—Au (Au content: 1 wt %) | 200 | 10000 | 40 | 27.3 | 14.7 | 85.3 | 23.2 |
| Example 7 | II: Cu—Zn—Al—Si—Au (Au content: 1 wt %) | 180 | 10000 | 40 | 26.7 | 63.3 | 36.7 | 9.8 |
| Example 8 | II: Cu—Zn—Al—Si—Au (Au content: 1 wt %) | 160 | 10000 | 40 | 17.4 | 79.9 | 20.1 | 3.4 |
| Example 9 | III: Cu—Zn—Al—Si—Pd (Pd content: 0.5 wt %) | 250 | 10000 | 40 | 31.0 | 34.8 | 65.2 | 20.2 |
| Example 10 | III: Cu—Zn—Al—Si—Pd (Pd content: 0.5 wt %) | 200 | 10000 | 40 | 29.3 | 14.8 | 85.2 | 24.9 |
| Example 11 | IV: Cu—Zn—Al—Si—Pd (Pd content: 0.25 wt %) | 250 | 10000 | 40 | 28.1 | 24.9 | 75.1 | 21.1 |
| Example 12 | IV: Cu—Zn—Al—Si—Pd (Pd content: 0.25 wt %) | 200 | 10000 | 40 | 26.2 | 14.0 | 86.0 | 22.6 |
| Example 13 | I: Cu—Zn—Al—Si—Pd (Pd content: 1 wt %) | 200 | 20000 | 40 | 23.7 | 13.4 | 86.6 | 20.5 |
| Example 14 | I: Cu—Zn—Al—Si—Pd (Pd content: 1 wt %) | 220 | 13000 | 70 | 47.6 | 11.8 | 88.2 | 41.9 |
| Example 15 | I: Cu—Zn—Al—Si—Pd (Pd content: 1 wt %) | 220 | 1000 | 70 | 28.2 | 15.1 | 84.9 | 23.9 |
| Example 16 | I: Cu—Zn—Al—Si—Pd (Pd content: 1 wt %) | 250 | 1000 | 70 | 33.8 | 25.4 | 74.6 | 25.2 |

TABLE 2

| | | reaction conditions | | | $CO_2$ | selectivity | | methanol |
|---|---|---|---|---|---|---|---|---|
| | Catalyst | T (° C.) | GHSV ($h^{-1}$) | P ($kg/cm^2$) | conversion rate (%) | CO (%) | methanol (%) | yield (%) |
| Comparative example 1 | V: Cu—Zn—Al—Si | 250 | 3600 | 40 | 16.2 | 40.6 | 59.4 | 9.6 |
| Comparative example 2 | V: Cu—Zn—Al—Si | 200 | 3600 | 40 | NR | NR | NR | NR |
| Comparative example 3 | VI: Cu—Zn—Al—Si—Zr—Ga | 250 | 3600 | 40 | 17.7 | 44.9 | 55.1 | 9.8 |
| Comparative example 4 | VI: Cu—Zn—Al—Si—Zr—Ga | 200 | 3600 | 40 | NR | NR | NR | NR |
| Comparative example 5 | VII: Cu—Zn—Al—Si—In (In content: 1 wt %) | 250 | 10000 | 40 | 20.5 | 32.4 | 67.6 | 13.8 |
| Comparative example 6 | VII: Cu—Zn—Al—Si—In (In content: 1 wt %) | 200 | 10000 | 40 | NR | NR | NR | NR |
| Comparative example 7 | VIII: Cu—Zn—Al—Si—Ce (Ce content: 1 wt %) | 250 | 10000 | 40 | 23.7 | 30.5 | 69.5 | 16.4 |
| Comparative example 8 | VIII: Cu—Zn—Al—Si—Ce (Ce content: 1 wt %) | 200 | 10000 | 40 | NR | NR | NR | NR |

Referring to Example 1 to Example 3 (i.e., Catalyst I: Cu—Zn—Al—Si—Pd (Pd content: 1 wt %)), Example 5 to Example 6 (i.e., Catalyst II: Cu—Zn—Al—Si—Au (Au content: 1 wt %)), and Comparative example 1 to Comparative example 8 (not modified with Pd or Au), when the temperature of the hydrogenation reaction is between about 200-250° C., Example 1 to Example 3, Example 5, and Example 6 obviously have higher $CO_2$ conversion rate, methanol selectivity, and methanol yield. That is, compared with Catalyst V that is not modified (Cu—Zn—Al—Si), Catalyst VI that is modified with Zr and Ga (Cu—Zn—Al—Si—Zr—Ga), Catalyst VII that is modified with In (Cu—Zn—Al—Si—In), and Catalyst VIII that is modified with Ce (Cu—Zn—Al—Si—Ce), Catalyst I (Cu—Zn—Al—Si—Pd) or Catalyst II (Cu—Zn—Al—Si—Au) that is modified with Pd or Au according to the examples of the present disclosure have better performance.

Moreover, referring to Example 4 (i.e., Catalyst I: Cu—Zn—Al—Si—Pd), Examples 7 and 8 (i.e., Catalyst II: Cu—Zn—Al—Si—Au), Comparative example 2 (i.e., Catalyst V: Cu—Zn—Al—Si), Comparative example 4 (i.e., Catalyst VI: Cu—Zn—Al—Si—Zr—Ga), Comparative example 6 (i.e., Catalyst VII: Cu—Zn—Al—Si—In), and Comparative example 8 (i.e., Catalyst VIII: Cu—Zn—Al—Si—Ce), when the temperature of the hydrogenation reaction is about 180° C., the hydrogenation reaction using Catalyst I that is modified with Pd (Cu—Zn—Al—Si—Pd) according to the example of the present disclosure is still reactive, and when the temperature of the hydrogenation reaction is about 160° C., the hydrogenation reaction using Catalyst II that is modified with Au (Cu—Zn—Al—Si—Au) according to the example of the present disclosure is still reactive; in contrast, when the temperature of the hydrogenation reaction is about 200° C., the hydrogenation reactions using Catalyst V that is not modified (Cu—Zn—Al—Si), Catalyst VI that is modified with Zr and Ga (Cu—Zn—Al—Si—Zr—Ga), Catalyst VII that is modified with In (Cu—Zn—Al—Si—In), and Catalyst VIII that is modified with Ce (Cu—Zn—Al—Si—Ce) do not produce methanol (i.e., unreacted). That is, by utilizing the catalyst provided by the examples of the present disclosure, the hydrogenation reaction may be carried out at a lower reaction temperature (e.g., the temperature of equipment in a general factory, about 180-250° C.). There is no need to provide additional thermal energy, thereby reducing production costs and process time, and improving efficiency of the process.

Furthermore, referring to Example 3 (i.e., Catalyst I: Cu—Zn—Al—Si—Pd (Pd content: 1 wt %)), Example 6 (i.e., Catalyst II: Cu—Zn—Al—Si—Au (Au content: 1 wt %)), Comparative example 6 and Comparative example 8 (not modified with Pd or Au), when the temperature of the hydrogenation reaction is about 200° C., the methanol yield of the hydrogenation reaction using Catalyst I that is modified with Pd (Cu—Zn—Al—Si—Pd) or Catalyst II that is modified with Au (Cu—Zn—Al—Si—Au) is greater than 20%; in contrast, when the temperature of the hydrogenation reaction is about 200° C., the hydrogenation reactions using Catalyst VII that is modified with In (Cu—Zn—Al—Si—In) and Catalyst VIII that is modified with Ce (Cu—Zn—Al—Si—Ce) do not produce methanol (i.e., unreacted). That is, a good methanol yield may be maintained at a lower reaction temperature by utilizing the catalyst according to the examples of the present disclosure.

Referring to Example 9 to Example 12, Catalyst III that is modified with Pd (Cu—Zn—Al—Si—Pd (Pd content: 0.5 wt %)) and Catalyst IV that is modified with Pd (Cu—Zn—Al—Si—Pd (Pd content: 0.25 wt %)) according to the examples of the present disclosure may still maintain good performance at a lower metal content (less than 1 wt %).

Moreover, referring to Example 13 to Example 16, under the conditions of different reaction temperatures, reaction pressures, or ratios of reactants (molar ratio of $H_2$ to $CO_2$), the Catalyst I that is modified with Pd (Cu—Zn—Al—Si—Pd) according to the example of the present disclosure has high reactivity.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the present disclosure. Thus, discussions of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize, in light of the description herein, that the disclosure can be practiced without one or more of the specific features or advantages of a particular embodiment. In other instances, additional features and advantages may be recognized in certain embodiments that may not be present in all embodiments of the disclosure.

What is claimed is:

1. A process for converting carbon oxide into methanol, the method comprising:
   putting a catalyst into a fixed bed reactor, the catalyst comprising 40-60 parts by weight of Cu, 25-40 parts by weight of Zn, 2-15 parts by weight of Al, 0.1-3 parts by weight of Si, and a metal comprising Au independently 0.1-5 wt % based on a total weight of Cu, Zn, Al, and Si in the catalyst, with the proviso that a total weight of Cu, Zn, Al, Si, and Au is 100 parts by weight; and
   introducing a gas mixture of hydrogen and the carbon oxide into the fixed bed reactor, and performing a hydrogenation reaction under the effect of the catalyst to form the methanol.

2. The process for converting carbon oxide into methanol as claimed in claim 1, wherein the carbon oxide comprises $CO_2$.

3. The process for converting carbon oxide into methanol as claimed in claim 1, wherein the hydrogenation reaction further forms CO and water.

4. The process for converting carbon oxide into methanol as claimed in claim 1, wherein the hydrogenation reaction is performed at a gas hourly space velocity of 3600-20000 $h^{-1}$.

5. The process for converting carbon oxide into methanol as claimed in claim 1, wherein the hydrogenation reaction is performed at a temperature of 180-250° C.

6. The process for converting carbon oxide into methanol as claimed in claim 1, wherein the hydrogenation reaction is performed under a pressure of 30-80 kg/cm$^2$.

7. The process for converting carbon oxide into methanol as claimed in claim 1, wherein a molar ratio of the hydrogen to the carbon oxide is 3/1 to 10/1.

8. The process for converting carbon oxide into methanol as claimed in claim 1, wherein the Au is 0.25-1 wt % based on the total weight of Cu, Zn, Al, and Si in the catalyst.

* * * * *